(12) United States Patent
Groos et al.

(10) Patent No.: US 8,490,492 B2
(45) Date of Patent: Jul. 23, 2013

(54) METHOD FOR NONDESTRUCTIVE TESTING OF PIPES

(75) Inventors: Andreas Groos, Rheurdt (DE); Stefan Nitsche, Mülheim (DE)

(73) Assignee: V & M Deutschland GmbH, Düsseldorf (DE)

( * ) Notice: Subject to any disclaimer, the term of this patent is extended or adjusted under 35 U.S.C. 154(b) by 299 days.

(21) Appl. No.: 12/673,883

(22) PCT Filed: Jul. 11, 2008

(86) PCT No.: PCT/DE2008/001151
§ 371 (c)(1),
(2), (4) Date: Jul. 27, 2011

(87) PCT Pub. No.: WO2009/024111
PCT Pub. Date: Feb. 26, 2009

(65) Prior Publication Data
US 2012/0125111 A1    May 24, 2012

(30) Foreign Application Priority Data
Aug. 17, 2007 (DE) .......................... 10 2007 039 382

(51) Int. Cl.
*G01N 29/04* (2006.01)
(52) U.S. Cl.
USPC ................... 73/618; 73/599; 73/600; 73/602; 73/622
(58) Field of Classification Search
USPC ................... 73/618, 598, 599, 600, 602, 622, 73/623, 627, 643
See application file for complete search history.

(56) References Cited

U.S. PATENT DOCUMENTS

| 4,641,531 | A |   | 2/1987  | Reeves et al. |         |
|-----------|---|---|---------|---------------|---------|
| 4,669,312 | A |   | 6/1987  | Maurer        |         |
| 4,679,437 | A | * | 7/1987  | Koike et al.  | 73/622  |
| 4,743,884 | A | * | 5/1988  | Parkins       | 340/297 |
| 5,085,082 | A |   | 2/1992  | Cantor et al. |         |
| 5,392,652 | A | * | 2/1995  | Levesque et al. | 73/629 |
| 6,332,361 | B1| * | 12/2001 | Yamada et al. | 73/627  |
| 7,263,887 | B2| * | 9/2007  | Sfeir et al.  | 73/602  |
| 7,975,549 | B2| * | 7/2011  | Fetzer et al. | 73/626  |

FOREIGN PATENT DOCUMENTS
WO    WO 03/016897 A    2/2003

* cited by examiner

*Primary Examiner* — J M Saint Surin
(74) *Attorney, Agent, or Firm* — Henry M. Feierisen LLC

(57) ABSTRACT

The invention relates to a process for the destruction-free testing of metallic pipes, in particular seamlessly produced steel pipes, in which method the entire length of the pipe is scanned following the circumference precisely and in this case, in addition to the wall thickness (WD) and the external diameter ($D_a$) being determined, the inner and outer surfaces of the pipe are examined for faults, the faults determined in this process are compared with a predefined permissible reference fault depth RFT (RFT=fault threshold of x% of the nominal wall thickness), the pipes are sent to reworking means if the fault threshold is exceeded, and a requisite minimum wall thickness ($WD_{min}$) has to be present in the reworked region after the processing has been carried out.

For this purpose, the invention provides for the pipes containing faults to be released for reworking only when the determined geometrical parameters have been correlated with one another beforehand in an evaluation step, and the following conditions are met: $WD-RFT>WD_{min}$ for faults on the inner and outer sides of the pipe and $D_a-RFT>D_{a\ min}$ for faults on the outer side of the pipe.

4 Claims, No Drawings

METHOD FOR NONDESTRUCTIVE TESTING OF PIPES

CROSS-REFERENCES TO RELATED APPLICATIONS

This application is the U.S. National Stage of International Application No. PCT/DE2008/001151, filed Jul. 11, 2008, which designated the United States and has been published as International Publication No. WO 2009/024111 and which claims the priority of German Patent Application, Ser. No. 10 2007 039 382.4, filed Aug. 17, 2007, pursuant to 35 U.S.C. 119(a)-(d).

BACKGROUND OF THE INVENTION

The invention relates to a method for nondestructive testing of pipes.

Nondestructive methods for testing metallic pipes for surface flaws, such as eddy current tests or ultrasound tests, are known for quite some time and have proven to be successful.

The ultrasound test is applied, for example, to monitor particularly the compliance of the pipe with the required wall thickness during production and to detect any discontinuities present in the pipe wall, such as laminations, cracks, notches, scrap marks or other surface flaws.

During the test, ultrasound pulses are excited in the wall according to the pulse-echo method starting at the exterior surface of the pipe, with the signals reflected at the interior surface of the pipe being received.

The thickness of the pipe wall can be calculated from the transit time of the signal and the sound velocity of the material to be tested. This method is typically used during production and automated for both magnetizable and non-magnetizable pipe materials.

This is done by accurately scanning the perimeter of the pipe over the entire pipe length. In addition to determining the wall thickness (WD) and the outside diameter ($D_a$), the interior and exterior surface of the pipe is also checked for flaws.

The known leakage flux test can also be used as an additional or alternative method for detecting surface flaws. The constant-field leakage flux test, which is predominantly employed for the detecting exterior flaws on the pipe wall, is used for pipes made of ferromagnetic steel to detect longitudinal discontinuities near the surface, such as cracks, scales, or bulges.

With these known nondestructive testing methods, the wall thickness and diameter of the pipe can be accurately measured and the perimeter of the pipe can be checked for flaws along the entire pipe length with a high resolution of several centimeters.

During the evaluation of the measurement values it is checked that a certain predetermined flaw threshold of x % of the nominal wall thickness (reference flaw depth, RFT) is not exceeded.

In a continuous manufacturing process used to produce, for example, seamless pipes, the flaws identified during the flaw test and marked on the pipe must be repaired, which is typically done during production by eradicating the flaw through grinding or milling.

However, certain conditions must be satisfied, because the wall thickness must not be less than a certain minimum wall thickness.

Hitherto, the identified flaws were initially ground either on the outside or on the inside of the affected pipe, whereafter the pipe was again moved through the test setup to verify, on one hand, that the pipe is now free of flaws and, on the other hand, that the required minimum wall thickness is maintained in the reworked flaw region, so that the pipe can be released.

With this approach, however, it can disadvantageously be ascertained only after mechanical machining and after subsequently repeating the test if the pipe is indeed free of flaws and has the required minimum wall thickness at the reworked location, or if the pipe needs to be cut or in extreme situations even scrapped.

This disadvantageous situation is due to the problem that in a continuous manufacturing process, the residual wall thickness can manually either not be determined at all or only with great difficulty.

For example, in a discontinuous production process, where the operating speed is less important, the wall thickness can be measured manually using ultrasound (US) at the location of a flaw to determine if reworking is feasible when taking into account the minimum wall thickness to be maintained.

This is, on one hand, quite time-consuming, which is unacceptable in a modern continuously operating production line and, on the other hand, requires additional personnel trained to perform these measurements.

SUMMARY OF THE INVENTION

It is an object of the invention to provide a reliable and cost-effective method for nondestructive testing of pipes, for example using ultrasound and/or leakage flux, that is capable of reliably determining, without performing a manual retest, if the remaining residual wall thickness is still sufficient for reworking the pipe in the region of the flaw, before a flaw identified on the pipe is actually reworked.

The object is solved in accordance with the invention by a method for nondestructive testing of metallic pipes, in particular of seamlessly produced steel pipes, wherein the perimeter of the entire length of the pipe is precisely scanned and, in addition to determination of the wall thickness and the outside diameter, the inner and outer surfaces of the pipe are examined for flaws and the identified flaws are compared with a predefined permissible reference flaw depth RFT (RFT =flaw threshold of x % of the nominal wall thickness), if the flaw threshold is exceeded, the pipes are sent for reworking, wherein a required minimum wall thickness must be present in the reworked region after reworking, wherein the pipes containing flaws are released for reworking only after the determined geometrical parameters have been correlated with one another in an evaluation step, and the following conditions are met:

$WD-RFT > WD_{min}$ for flaws on the inside and outside of the pipe, and $D_a-RFT > D_{a\,min}$ for flaws on the outside of the pipe.

With the test method according to the invention, the perimeter of the pipe is accurately scanned along the entire pipe length, whereby not only the wall thickness (D) and the outside diameter ($D_a$) are determined, but the interior and exterior surfaces of the pipe are also examined for flaws.

The detected flaws are compared with a predetermined allowable reference flaw depth RFT (RFT=flaw threshold of x % of the nominal wall thickness). If the flaw threshold is exceeded, the flaws are reworked, with the requirement that the minimum wall thickness ($WD_{min}$) required in this region must still be present after reworking.

According to the invention, the flaws are allowed to be reworked only when the following conditions are satisfied:

$WD-RFT > WD_{min}$ for flaws on the inside and outside of the pipe, and $D_a-RFT > D_{a\,min}$ for flaws on the outside of the pipe.

With the method of the invention, it can now advantageously be determined by a nondestructive test of the pipes during production, either while the actual test is performed or immediately thereafter, if reworking of a flaw is feasible when the minimum wall thickness to be maintained is taken into consideration.

The costs associated with unnecessary reworking and unneeded tests can be safely eliminated by identifying and removing those pipes that can no longer be reworked early in the process.

According to an advantageous modification of the invention, if the flaws are identified and reworked in separate production lines, a respective coordinate system zero can be marked on the pipe to enable the rework station to correctly associate the flaw on the pipe surface. The same applies in situations where determination of wall thickness/outside diameter and the flaw test are performed in separate process lines.

BRIEF DESCRIPTION OF THE DRAWING

None

DETAILED DESCRIPTION OF PREFERRED EMBODIMENTS

The invention will now be described in more detail with reference to two variants of the method:

Variant 1:

The wall thickness (WD) and the outside diameter ($D_a$) are known at each point of the pipe surface from the nondestructive measurements. If the flaw threshold set for x % of the nominal wall thickness (RFT, reference flaw thickness) is exceeded, then it is checked if the following conditions are met:

WD−AFT>$WD_{min}$ for flaws on the inside and outside of the pipe, and $D_a$−AFT>$D_{a\ min}$ for flaws on the outside of the pipe.

If this is the case, then the pipe is released to start rework of the flaw.

If the conditions are not met, then the respective location is separately marked and is not reworked, because reworking would cause the wall thickness and/or the outside diameter to fall outside the tolerance range.

If the wall thickness of the pipe has only approximately the minimum wall thickness, then indications below the reference flaw threshold can continue to be evaluated in these regions. If the computed "flaw-free residual wall thickness" falls below the minimum wall thickness ($WD_{min}$), then the pipe must be rejected.

Variant 2:

In this variant, in first approximation, a linear relationship between the flaw depth and flaw amplitude is assumed. The wall thickness (WD) and the outside diameter ($D_a$) are known at each point on the pipe surface.

If the flaw threshold is set to x % of the nominal wall thickness (RFT=reference flaw thickness, AFT=flaw thickness, computed from (flaw amplitude of the actual display)/(amplitude of the reference flaw)×(depth of the reference flaw)) and this flaw threshold is exceeded, then it is checked if the following conditions are satisfied:

WD−AFT>$WD_{min}$ for flaws on the inside and outside of the pipe, and $D_a$−AFT>$D_{a\ min}$ for flaws on the outside of the pipe.

If this is the case, then the pipe is released to start rework of the flaw.

If the condition is not met, then the respective location is separately marked and is not reworked, because reworking would cause the wall thickness and/or the outside diameter to fall outside the tolerance range.

According to an advantageous modification of the invention, the method can be optimized further. If one of the above conditions is still satisfied (i.e., residual wall thickness/outside diameter are still okay) at a location where the flaw threshold is exceeded, then it is displayed at the reworking site how much material can still be removed from the wall thickness, before the pipe is outside the permitted tolerances ($WD_{min}$, $D_{a\ min}$).

In an advantageous embodiment of the invention, subsequent processing of flaws on the pipes can be automated.

If a flaw to be reworked is identified, material is removed at the location of the flaw by a fully-automated processing system through grinding, milling and the like, until the minimum tolerance limit ($WD_{min}$, $D_{a\ min}$) is reached, whereafter the pipe is rechecked in the test station.

The important properties of the method of the invention can be summarized as follows:
- Determination of the wall thickness/outside diameter and the depth of a flaw with high resolution,
- Correlation of these measurement values via local coordinates,
- Calculation of residual wall thickness/residual outside diameter based on the following assumptions:
  - The depth of a flaw is proportional to the amplitude of a flaw at least in the region around the reference flaw depth used for adjustments (e.g., for methods such as ultrasound, leakage flux, eddy currents, etc.).
  - Alternatively, it will be assumed that a natural defect with an amplitude that reaches/exceeds the reference flaw threshold has at least the same flaw depth as the reference flaw.
- Automatic decision about repair/scrapping based on the aforementioned criteria.

The advantages of the invention are summarized:
Reduced repair and testing costs,
Higher throughput in the finishing line,
Possible complete automation of the flaw rework process.

What is claimed is:

1. A method for nondestructive testing of a metallic pipe, in particular of a seamlessly produced steel pipe, comprising the steps of:
   scanning a perimeter of the pipe along an entire length of the pipe;
   determining from the scan a wall thickness and an outside diameter;
   examining an inner and outer surface of the pipe to identify flaws;
   comparing the identified flaws with a predefined permissible reference flaw depth expressed as a percentage of a nominal wall thickness of the pipe;
   correlating the wall thickness, the outside diameter and the permissible reference flaw depth with one another in an evaluation step; and
   releasing the pipes for reworking only if the correlation satisfies the following condition:
   WD−RFT>$WD_{min}$ for flaws on an inside and outside of the pipe, and
   $D_a$−RFT>$D_{a\ min}$ for flaws on the outside of the pipe,
   wherein
   WD=wall thickness,
   $WD_{min}$=required minimum wall thickness,
   $D_a$=outside diameter of the pipe,
   $D_{a\ min}$=required minimum outside diameter of the pipe,
   RFT=reference flaw depth.

2. The method of claim 1, further comprising the steps of:
by assuming a linear relationship between a displayed flaw amplitude and an actual flaw depth, computing the actual flaw depth according to the following formula:
AFT=(displayed flaw amplitude)/ (reference flaw amplitude)×(reference flaw depth), and
releasing the pipes for reworking only if the following conditions are satisfied:
WD−AFT>WDmin for flaws on the inside and outside of the pipe, and
Da−AFT>Da min for flaws on the outside of the pipe,
wherein AFT is the actual flaw depth.

3. The method of claim 1, wherein the pipes are released for reworking automatically.

4. The method of claim 1, further comprising the step of applying on the pipes having an identified flaw a coordinate system zero that unambiguously localizes a corresponding location of the flaw.

\* \* \* \* \*

UNITED STATES PATENT AND TRADEMARK OFFICE
CERTIFICATE OF CORRECTION

PATENT NO. : 8,490,492 B2  
APPLICATION NO. : 12/673883  
DATED : July 23, 2013  
INVENTOR(S) : Andreas Groos et al.

Page 1 of 1

It is certified that error appears in the above-identified patent and that said Letters Patent is hereby corrected as shown below:

Title page, item (74) Attorney, Agent, or Firm "Feierisen LLC" should correctly be spelled --Feiereisen LLC--.

Signed and Sealed this
Seventeenth Day of September, 2013

Teresa Stanek Rea
*Deputy Director of the United States Patent and Trademark Office*